United States Patent [19]

Grenier

[11] Patent Number: 5,524,041
[45] Date of Patent: * Jun. 4, 1996

[54] RADIATION COLLIMATOR SYSTEM

[75] Inventor: Raymond P. Grenier, Milwaukee, Wis.

[73] Assignee: Scinticor, Inc., Milwaukee, Wis.

[*] Notice: The portion of the term of this patent subsequent to May 10, 2011, has been disclaimed.

[21] Appl. No.: 105,800

[22] Filed: Aug. 12, 1993

Related U.S. Application Data

[63] Continuation of Ser. No. 605,721, Oct. 29, 1990, Pat. No. 5,239,568.

[51] Int. Cl.$^6$ ................................ G21K 1/02; A61B 6/00
[52] U.S. Cl. ....................... 378/147; 378/149; 378/154; 250/363.1; 250/505.1; 128/653.1
[58] Field of Search .................................. 378/147, 149, 378/4, 154; 250/363.02, 363.04, 505.1; 128/653.1

[56] References Cited

U.S. PATENT DOCUMENTS

| | | | |
|---|---|---|---|
| 3,257,560 | 6/1966 | Jones . | |
| 3,781,564 | 12/1973 | Lundberg | 250/505 |
| 4,054,800 | 10/1977 | Leask | 250/505 |
| 4,096,389 | 6/1978 | Ashe et al. | 250/445 |
| 4,125,776 | 11/1978 | Tosswill et al. | 250/508 |
| 4,194,123 | 3/1980 | Wittry | 250/492 |
| 4,212,707 | 7/1990 | Tosswill et al. | 204/26 |
| 4,277,684 | 7/1981 | Carson | 378/149 |
| 4,295,047 | 10/1981 | Koga et al. | 378/4 |
| 4,419,585 | 12/1983 | Strauss et al. | 250/505 |
| 4,465,540 | 8/1984 | Albert | 156/252 |
| 4,582,999 | 4/1986 | Dance et al. | 378/147 |
| 4,672,648 | 6/1987 | Mattson | 378/149 |
| 4,682,033 | 7/1987 | Martin et al. | 250/363.02 |
| 4,825,454 | 4/1989 | Annis et al. | 378/147 |
| 4,852,142 | 7/1989 | Pillay et al. | 378/145 |
| 4,875,227 | 10/1989 | Rossi et al. | 378/154 |
| 4,951,305 | 8/1990 | Moore et al. | 378/147 |
| 5,003,980 | 4/1991 | Loo et al. | 378/89 |
| 5,024,233 | 6/1991 | Simecek et al. | 128/659 |
| 5,099,134 | 3/1992 | Hase et al. | 378/149 |
| 5,103,823 | 4/1992 | Acharya et al. | 250/363.04 |
| 5,198,680 | 3/1993 | Kurakake | 378/147 |
| 5,231,654 | 7/1993 | Kwasnick et al. | 378/147 |
| 5,239,568 | 8/1993 | Grenier | 378/147 |
| 5,309,911 | 5/1994 | Grenier | 128/653.1 |

OTHER PUBLICATIONS

Article "Dectectors & Instruments for Nuclear Spectroscopy", 1980.

Primary Examiner—Georgia Y. Epps
Assistant Examiner—Kim-Kwok Chu
Attorney, Agent, or Firm—Reinhart, Boerner, Van Deuren, Norris & Rieselbach

[57] ABSTRACT

A collimator assembly for removing selected radiation output from a specimen. The assembly includes collimator elements with each element having walls comprised of a first material covered by an inner layer of a second material which preferentially absorbs inelastic scattered radiation created in the first material.

16 Claims, 12 Drawing Sheets

$a - c = 2t$
$\quad\quad = 0.5 MM$
$b - a = 2t'$
$\quad\quad = 0.3 MM$

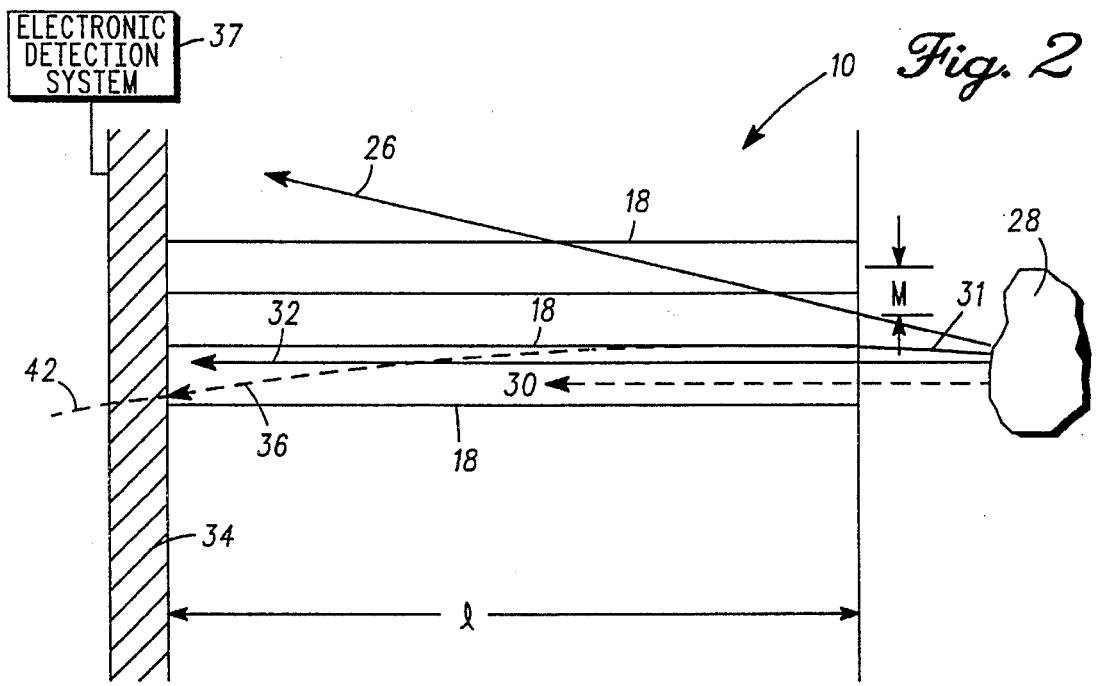
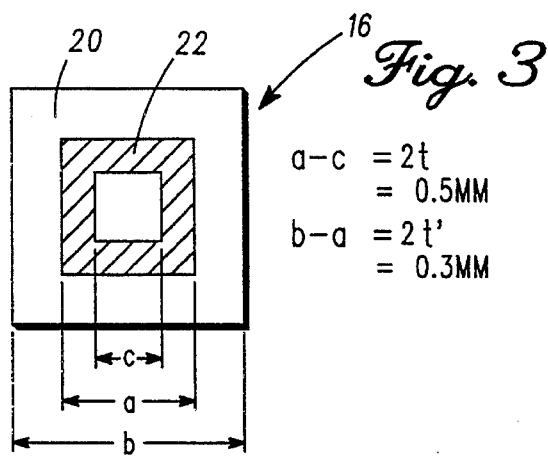
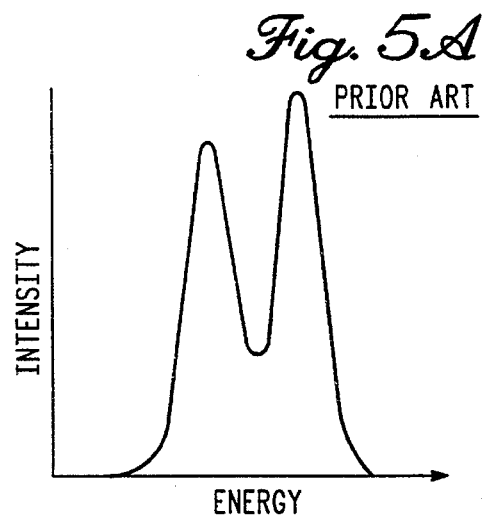
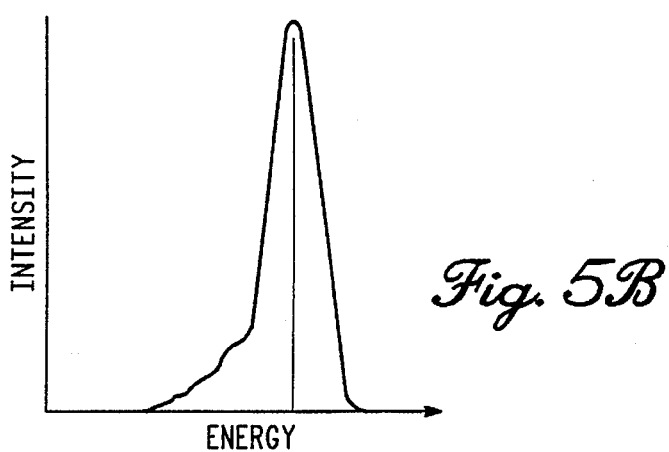

Fig. 6

| B SVC 0.75 | RA 1.5 | RA RAV 2.25 | RA RV PA 3.0 | RH RL 3.75 | PA RL LL 4.5 | PA L 5.25 |
|---|---|---|---|---|---|---|
| PA L 6.0 | L 6.75 | L 7.5 | L LA 8.25 | L LA LV 9.0 | L LA LV 9.75 | LA LV AO 10.5 |
| LV AO AT 11.25 | LV AO AT 12.0 | LV AO AT 12.75 | LV AO DA 13.5 | LH 14.25 | LH 15.0 | LH 15.75 |
| LH 16.5 | LH 17.25 | LH 18.0 | LH MY 18.75 | LH MY 19.5 | LH RH 20.25 | LH RH 21.0 |
| RC 21.75 | RC 22.5 | RC 23.25 | RC 24.0 | RC 24.75 | RC 25.5 | RC 26.25 |

RADIATION COLLIMATOR SYSTEM

BACKGROUND OF THE INVENTION

This invention is a continuation of a U.S. application Ser. No. 07/605,721, filed Oct. 29, 1990, now U.S. Pat. No. 5,239,568, issued on Aug. 24, 1993.

This invention generally concerned with a collimator for removing unwanted divergent beams of radiation received from a source, leaving a well resolved radiation beam for detection and analysis. More particularly, the invention is directed to a collimator having a layered structure for removing not only unwanted angularly divergent radiation beams, but also for removing radiation inelastically scattered by the collimator structure itself.

Radiographic imaging methods and apparatus are undergoing rapid evolution as efforts are being made to improve the ability to image selected portions of a specimen or diffract and sense radiation from the specimen. The effectiveness of these various methodologies and even the ability to use certain techniques depends primarily on spatial resolution and on the associated signal to noise ratio in the data being accumulated. Present technology is able to generate a radiation intensity adequate to image and evaluate structure and analyze a number of abnormalities. However, current technology cannot effectively collimate this radiation intensity without counting certain divergent radiation and thus including substantial unwanted noise in the resulting data. Such divergent, unwanted signal derives, for example, from radiation which has been inelastically scattered from the collimator structure itself. This deficiency therefore requires exposing the specimen to larger intensities of radiation in order to achieve a desired resolution. Unfortunately, such increased radiation exposure can be hazardous, and moreover there are some divergent radiation sources whose deleterious effects cannot be alleviated even by increasing the radiation signal level.

It is therefore an object of the invention to provide an improved method of manufacture and method for collimation of radiation.

It is another object of the invention to provide a new method of manufacture of a collimator for a radiation beam.

It is a further object of the invention to provide an improved collimating device for removing divergent radiation beams received from, or passed through, a specimen undergoing diagnostic analysis.

It is an additional object of the invention to provide a new radiation collimator assembly for providing highly resolved, high intensity data characteristic of a specimen but without having to increase exposure to radiation.

It is yet another object of the invention to provide an improved radiation collimator assembly having a layered wall material structure for substantially reducing inelastic scattered radiation present in the detected data signal.

It is still a further object of the invention to provide a new collimator having a lead base structure with an outer layer of a material which preferentially absorbs X-rays generated from inelastic scattering of gamma rays from the lead base collimator structure.

It is yet an additional object of the invention to provide a radiation collimator having a selectable collimator length using a stack of different predetermined height collimator units.

It is still a further object of the invention to provide a gamma ray collimator of lead with a thin tin layer on the collimator walls to absorb lead X-rays generated by inelastic gamma ray scattering from the lead collimator.

Other objects, features and advantages of the present invention will be readily apparent from the following description of the preferred embodiments thereof, taken in conjunction with the accompanying drawings described below wherein like elements have like numerals throughout the several views.

DESCRIPTION OF THE DRAWINGS

FIG. 2 shows a side view of a cross section of a single vertical stack of collimators;

FIG. 3 illustrates a top, or face, view of one embodiment of a collimator;

FIG. 5A illustrates the detected radiation spectra from a cobalt radionuclide source using a conventional lead collimator assembly and FIG. 5B shows the radiation spectra using the layered lead-tin collimator assembly of the invention; and FIG. 6 shows a chart of the explanation key for each block of a matrix of a time lapse photographs of a patient's cardiac system;

DETAILED DESCRIPTION OF PREFERRED EMBODIMENTS

Figure 1:
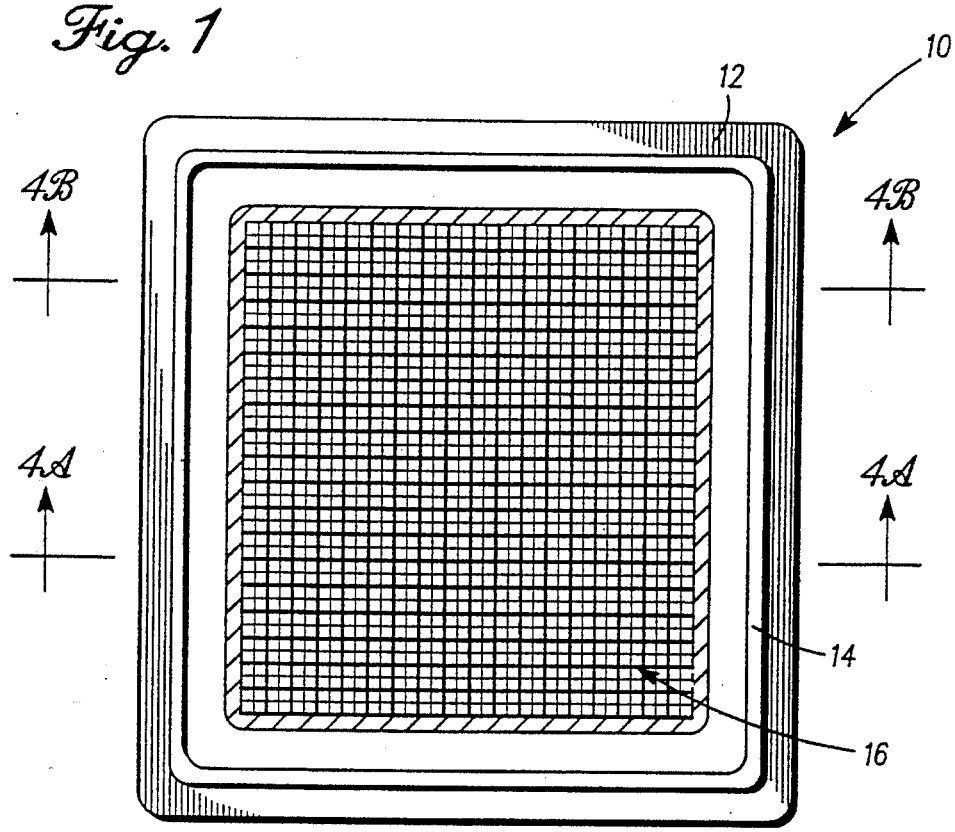
FIG. 1 shows an incident radiation view of a collimator assembly.

A gamma ray collimator assembly constructed in accordance with the invention is shown generally at 10 in FIG. 1.

Figure 4A:
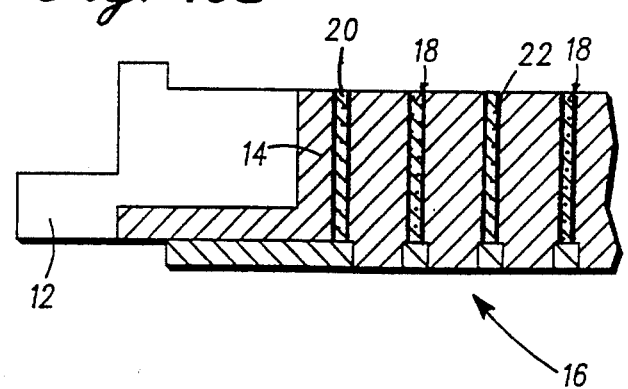
FIG. 4A shows a cross section taken along line 4A—4A in FIG. 1
Figure 4B:
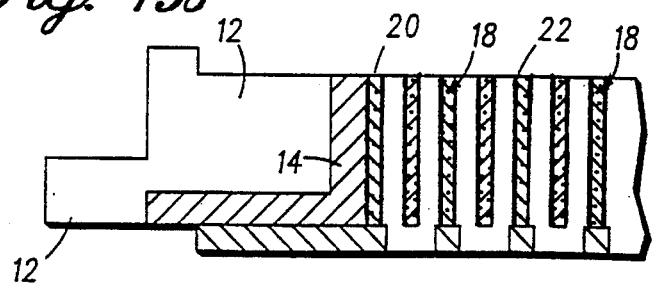
FIG. 4B shows a cross section taken along line 4B—4B in FIG. 1.
Figure 7:
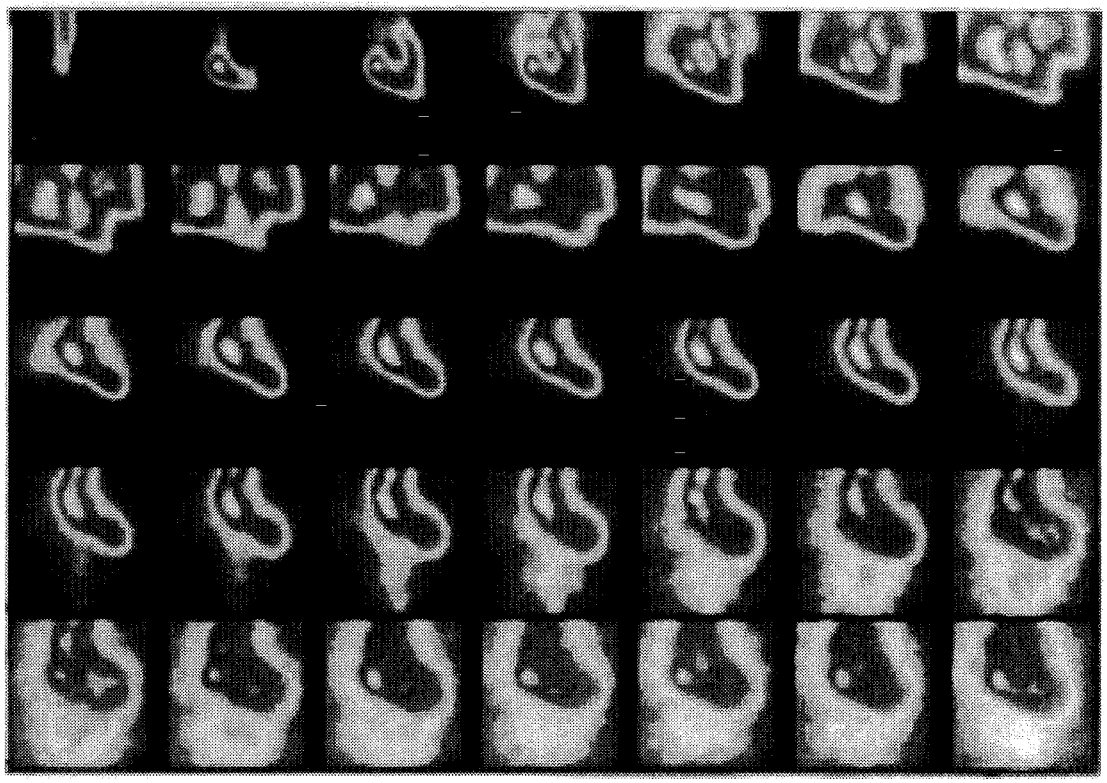
FIG. 7 shows an example time lapse photograph for a matrix of photograph of a patient's cardiac system in a radionuclide angiographic (RNA) study.
Figure 8A:
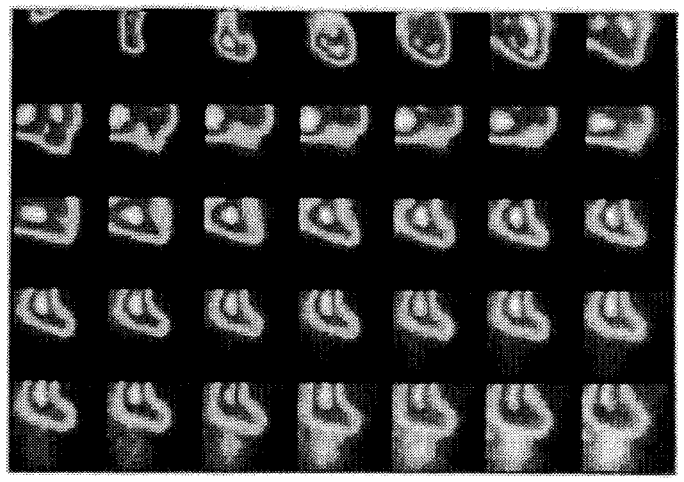
FIG. 8A shows an RNA study for a patient Beau using a conventional lead collimator and FIG. 8B shows an RNA study for patient Beau using a tin/lead collimator form of the invention.
Figure 8B:
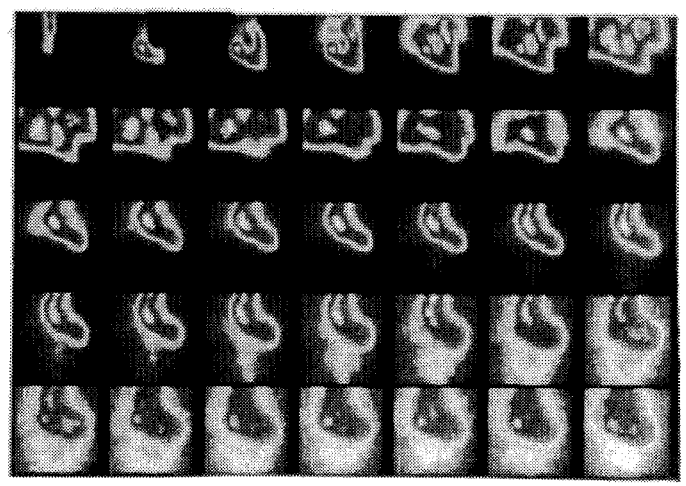
Figure 9A:
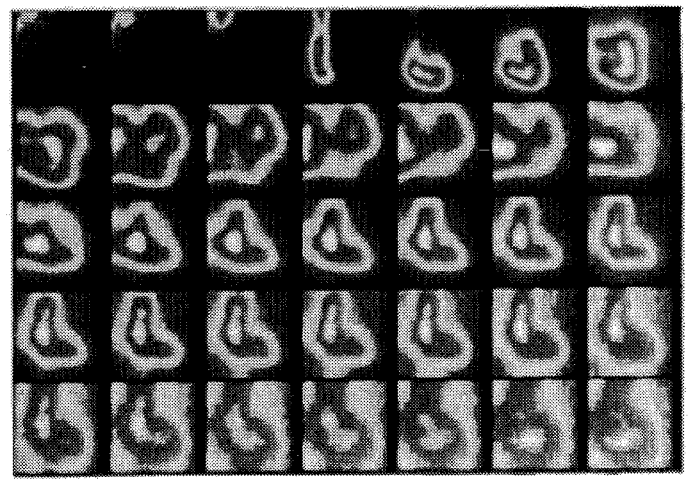
FIG. 9A shows an RNA study for a patient Cul using a conventional lead collimator and FIG. 9B shows an RNA study for patient Cul using a tin/lead collimator form of the invention.
Figure 9B:
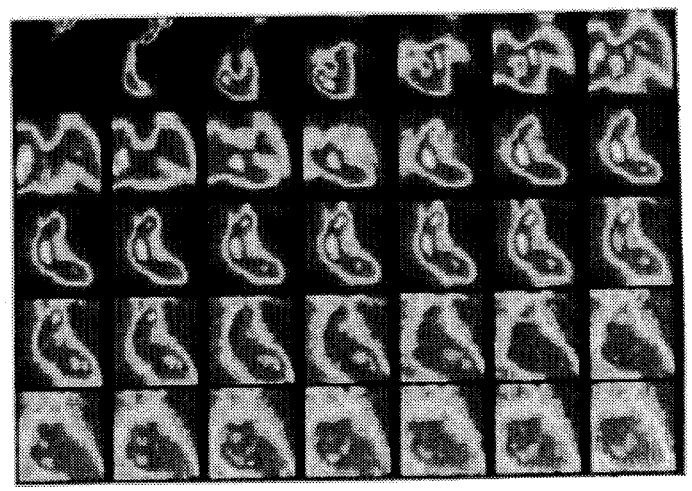
Figure 10A:
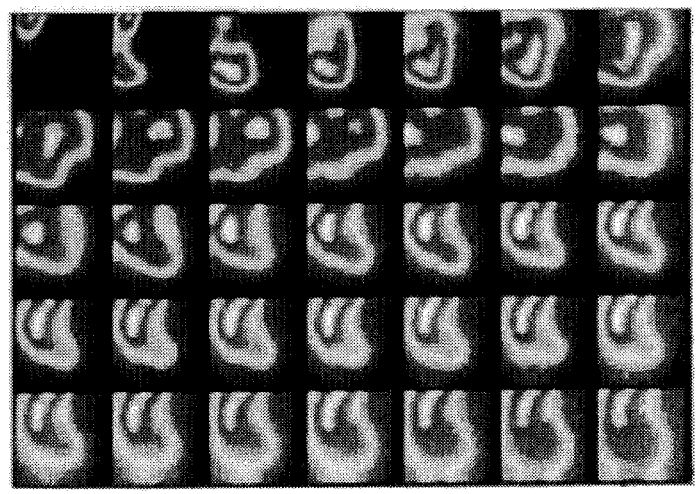
FIG. 10A shows an RNA study for a patient Rose using a conventional lead collimator and FIG. 10B shows an RNA study for patient Rose using a tin/lead collimator form of the invention.
Figure 10B:
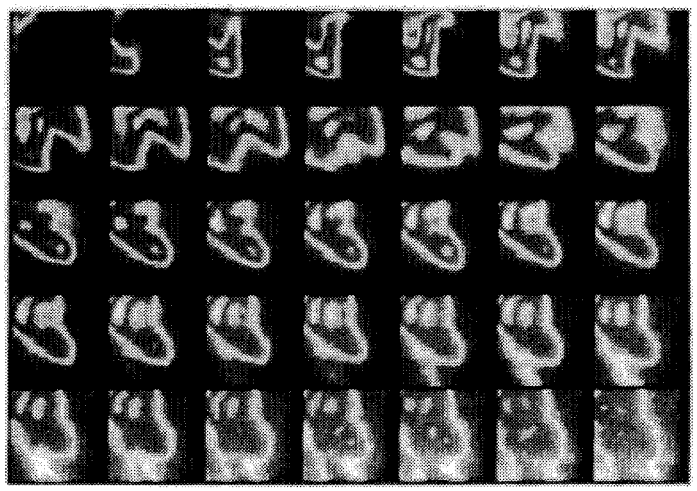
Figure 11A:
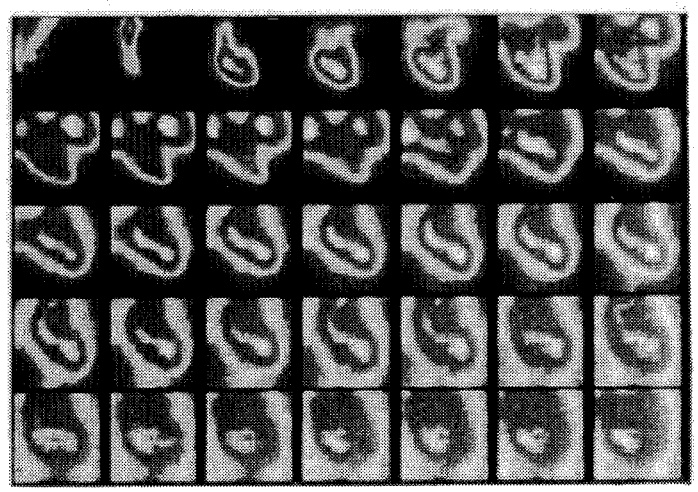
FIG. 11A shows an RNA study for a patient Badu using a conventional lead collimator and FIG. 11B shows an RNA study for patient Badu using a tin/lead collimator form of the invention.
Figure 11B:
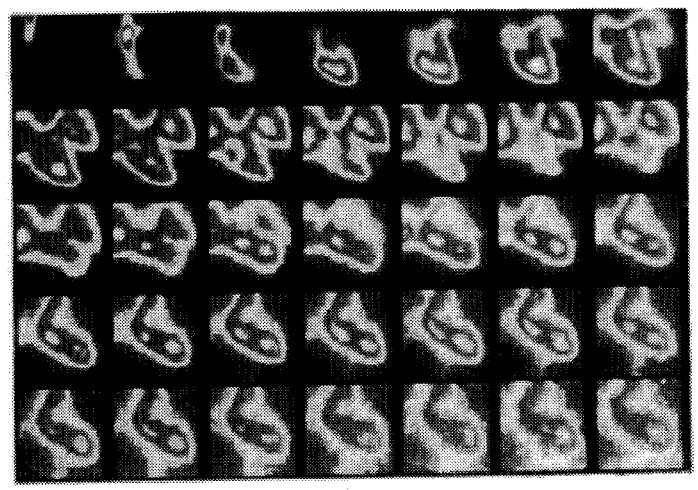
Figure 12A:
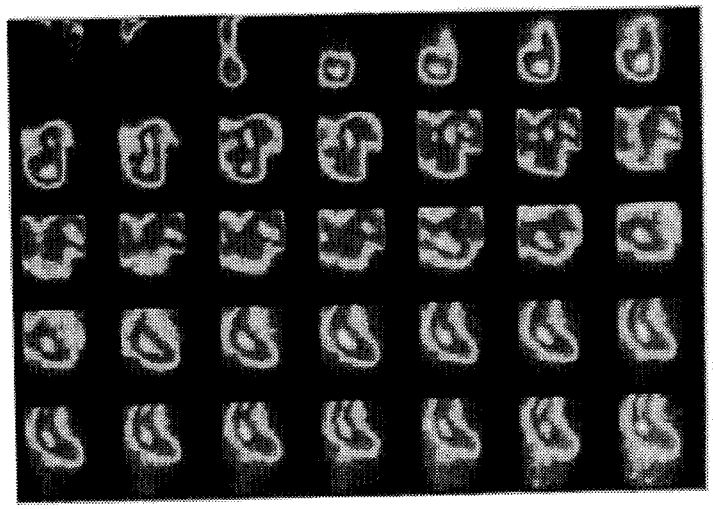
FIG. 12A shows an RNA study for a patient Quag using a conventional lead collimator and FIG. 12B shows an RNA study for patient Quag using a tin/lead collimator form of the invention.
Figure 12B:
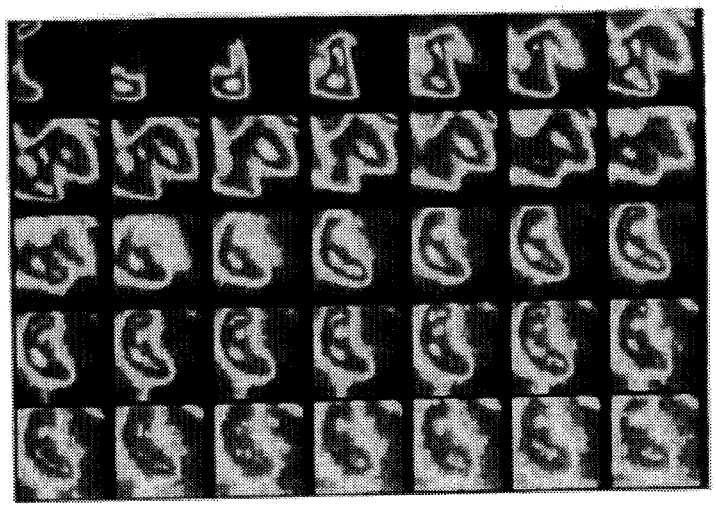
Figure 13A:
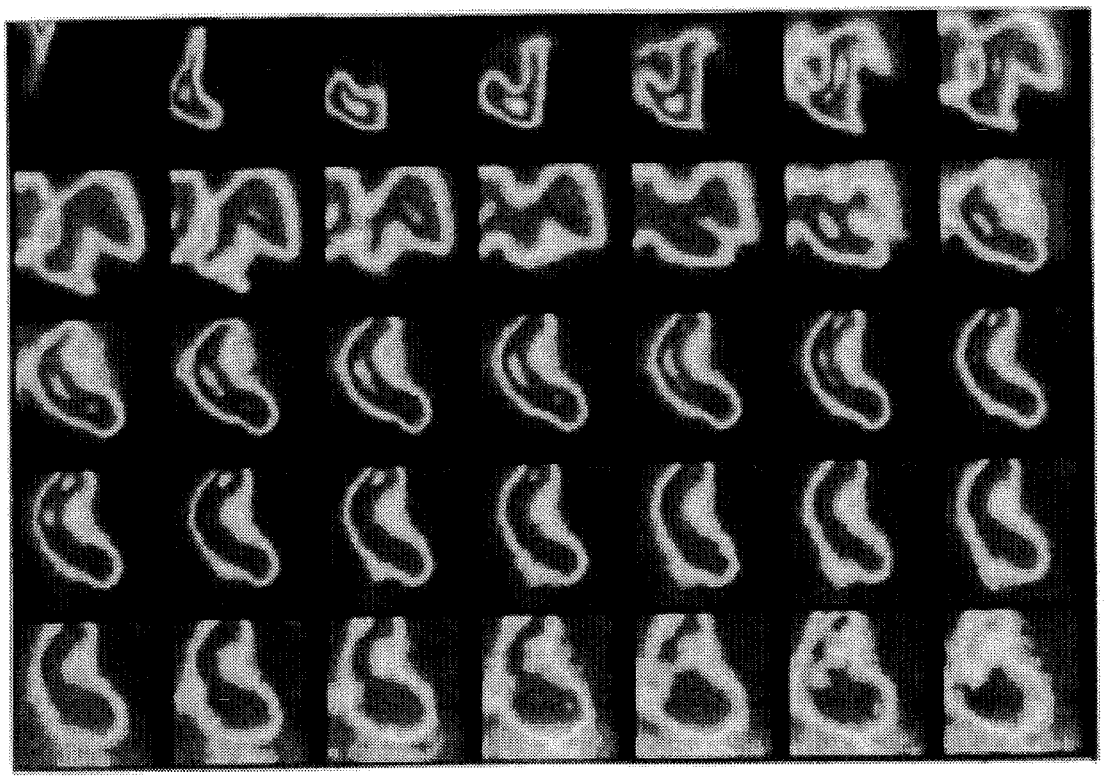
FIG. 13A shows an RNA study for a patient Char using a high resolution lead collimator.
Figure 13B:
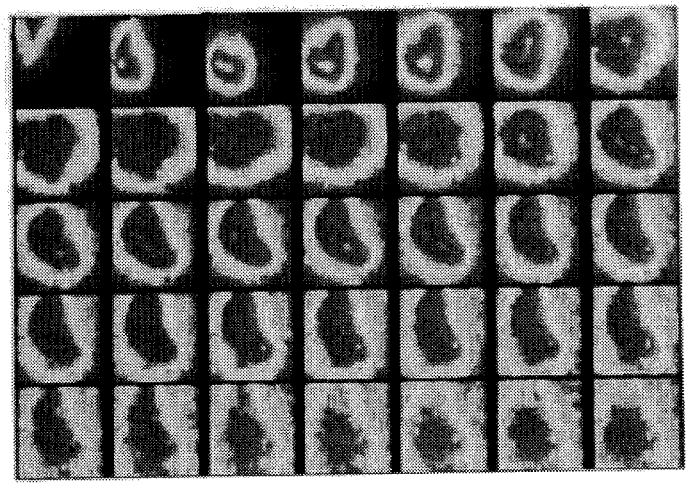
FIG. 13B shows a study for the patient performed using a simultaneous dual energy method, and 13C shows an RNA study for the patient Char using a tin/lead collimator form of the invention.
Figure 13C:
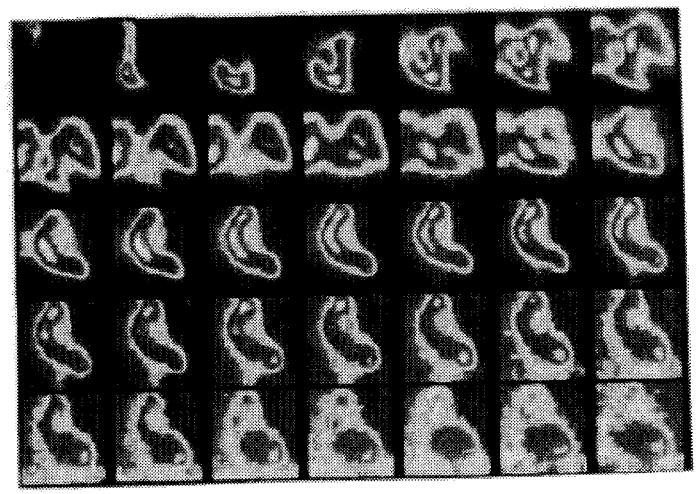
Figure 14A:
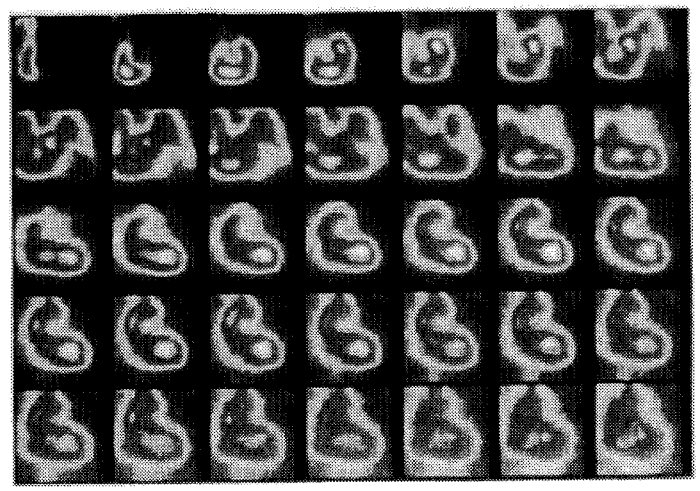
FIG. 14A shows an RNA study for a patient Mel using a conventional lead collimator and FIG. 14B shows an RNA study performed using a slow bolus mode with a tin/lead collimator form of the invention.
Figure 14B:
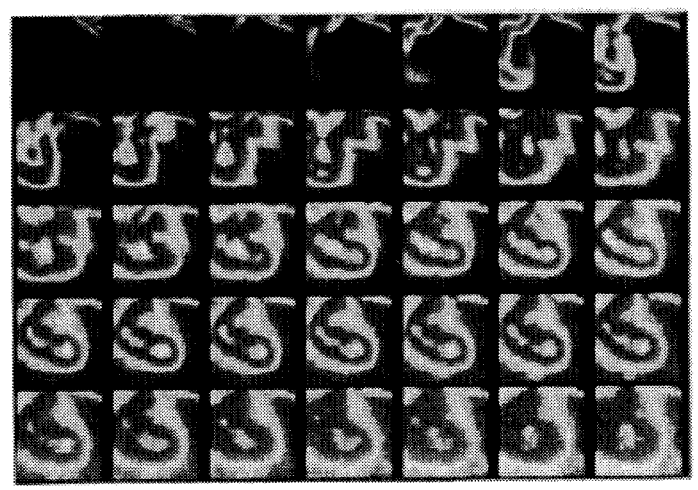

The collimator assembly 10 includes a housing 12, typically constructed of aluminum. Coupled to the housing 12 is a side shielding 14 which is normally constructed of lead when the collimator assembly 10 is used for collimation of gamma rays. Disposed within the housing 12 and coupled to the side shielding 14 are collimator elements 16 constructed of collimator walls 18 (best seen in FIGS. 2–4).

In a preferred embodiment the collimator walls 18 are constructed of a layered material with a base material structure 20 and a thin layer 22 disposed thereon (see FIGS. 2 and 3). The radiation used in a conventional radiographic embodiment is high energy X-rays or gamma rays, and in a preferred embodiment the base material structure 20 is lead and the thin layer 22 is tin. For example, as shown in FIG. 3 in a preferred geometry the collimator walls 18 are square cross section tubing with lead being the base material structure 20 (hereinafter "lead structure 20") and tin being the thin layer 22. The tin can be readily coupled to the lead structure 20 by conventional methods such as electroplating, evaporation, ion deposition and mechanical lamination.

Operation of the collimator assembly 10 is best illustrated in FIG. 2. In this example, the radiation is gamma radiation, and gamma rays 26 originate from a conventional radionuclide source, such as cobalt, thallium or technitium, which is passed through a specimen 28 (depicted schematically). As the radioactive radionuclide source decays it emits characteristic gamma rays which are emitted from or pass through the specimen 28 and form an image, such as, for example, in conventional "first pass" angiography. For example, see copending patent application Ser. No. 07/409,249, filed Sep. 19, 1989, now U.S. Pat. No. 5,103,823, assigned to the instant assignee and is incorporated by reference herein.

Other radiations can also be used in combination with the collimator assembly 10 such as, ions, neutrons, positrons, X-rays, electrons and the like. A desired gamma ray portion 30 of the gamma rays 26 travel along a substantially parallel line 32 or within a very narrow angular range within which the gamma ray portion 30 does not strike the collimator assembly 10. The desired gamma ray portion 30 thus passes undisturbed through the collimator assembly 10. This desired gamma ray portion 30 is sensed by a conventional detector 34, such as, a gamma ray counter of a conventional Anger camera or a sensor of a first pass cardiac inspection system, such as the angiographic system of Scinticor Incorporated of Milwaukee, Wis.

In addition to the desired gamma ray portion 32, having a substantially unchanged primary energy $E_0$ after emission from the radiation source, there is a substantial fraction of divergent gamma rays 31 from the specimen 28. These divergent gamma rays 31 interact with the collimator walls 18 and result in diminished resolution of spatial features of the specimen 28. The desirability of removing such divergent gamma rays 31 is well known. For example, in U.S. Pat. No. 4,096,389 (which is incorporated by reference herein) the benefits of effective collimation, generally, are described for X-ray and gamma ray radiographic imaging technology. Such advantages also are apparent for other conventional radiographic systems, such as in emission tomography systems and Anger camera geometries (see, for example, U.S. Pat. Nos. 4,295,047; 4,682,033; 4,852,142; 4,672,648; and 4,277,684, which are incorporated by reference herein).

The divergent gamma rays 31 interact with the collimator walls 18 and the divergent gamma rays 31 lose energy, creating inelastic scattered radiation 36 having energies less than $E_0$ of the initial gamma rays 26. In order to achieve optimum resolution, the divergent gamma rays 31 (and the inelastic scattered byproduct radiation) should be substantially removed by the collimator assembly 10. Removal of the inelastic scattered radiation 36 would allow sensing and analysis of only the desired gamma ray portion 30 which is substantially parallel to line 32 in FIG. 2 and includes undisturbed gamma rays 30 from the specimen 28. This desired gamma ray portion 30 is then sensed by detector 34. This enables achieving the desired level of resolution for the features of the specimen 28.

As mentioned hereinbefore, the divergent gamma rays 31 before interaction with the collimator walls 18 have an energy of $E_0$, and after wall interaction the inelastic scattered radiation 36 includes a range of electromagnetic wave energies, from $E_0$ at a maximum to lesser values. In the case of an inelastic interaction, the divergent gamma rays 31 interact with the lead structure 20 of the collimator assembly 10. When the gamma rays 31 (such as, cobalt radionuclide gamma rays having an energy of roughly 140 KeV) enter the lead structure 20, energy can be lost by a variety of processes. For example, energy can be lost by excitation of electrons from the ground state in each of the lead atoms. These excited electrons return to their ground state energy level and simultaneously emit a characteristic X-ray, such as Pb K-alpha radiation having an energy of about 74 KeV. Numerous ocher electron excitations and decays to ground state occur, giving rise to lower energy X-rays and other electromagnetic wave species which are preferentially absorbed within the lead structure 20. These events normally occur without reemitting any X-rays into the collimator free space outside the lead structure 20, and thus the lower energy radiation is not normally detected by the detector 34.

Therefore, as stated above, when the divergent gamma rays 31 enter the lead structure 20, a 74 KeV X-ray can escape into free space as a consequence of inelastic scattering of the 140 KeV cobalt gamma ray. This emitted 74 KeV inelastic scattered X-ray 36 travels along line 42 (see FIG. 2) and is sensed by the detector 24. Conventional energy discriminators in an electronic detection system 37 (shown schematically), which is coupled to the detector 34, can remove the unwanted signal arising from the inelastic scattered X-ray 36. However, such a sensed event can cause substantial loss of resolution which is detrimental to spatial (or angular) resolution. This loss of resolution can result because the event is still counted by the counter 34 and prevents detection of the desired undeviated gamma ray portion 32. Conventional counter electronics in the detection system 37 can only count at a given finite rate, such as, for example, 100,000 to 1,000,000 counts per second, and detection of unwanted energetic photons (or particles) prevents accumulating a desired event. The need to maximize useful signal (coupled with the limits on the ability of the electronics to count all incoming events) makes it imperative to remove the emitted, or inelastically scattered, X-rays 36 in order to use the full capacity of the counter 34 to sense the desired gamma ray portion 30.

In FIGS. 2 and 3 is shown the layered wall structure of the collimator assembly 10. This layered wall structure enables detection of substantially only the gamma rays 30 and by removal of the unwanted inelastic scattered X-rays 36 so such a component is not sensed by the detector 34. As shown in the preferred embodiment, the thin layer 22 is tin but can be any material which exhibits a large absorption coefficient for the energetic inelastic scattered X-rays 36 emitted from the underlying lead structure 20. The tin layer 22 can be quite thin (for example, about ¼ mm) and still be quite effective in absorbing the inelastic scattered lead K-alpha X-rays 36. As can be understood from conventional X-ray optics (and other appropriate spectroscopic sciences, such as ion optics) the only portion of energetic photons which might be sensed by the detector 34 is emitted primarily at relatively small angles with respect to the line 32. The geometry of tile collimator assembly 10, including the length "l" in FIG.2 and the other dimensions (see FIG. 3) result in the reemitted inelastic scatterd X-rays 36 traveling over a substantial path length within the tin layer 22. As a consequence of the large path length travelled at such small angles relative to direction 32, and the well known exponential absorption attenuation, the tin layer 22 is very effective in removing the unwanted inelastic scattered X-rays 36. The ratio of transmitted intensity to initial intensity is exp $(-\mu \cdot t)$, where $\mu$ is the well known linear absorption coefficient of tin (about 28.1 $cm^{-1}$ at 75 Kev), and "t" is the path length travelled by the inelastic scattered X-rays 36 in the tin layer.

The effect of the collimator assembly 10 on reducing the X-rays 36 is demonstrated dramatically by comparing FIGS. 5A and 5B. FIG. 5A shows the radiation sensed by the detector 34 in a Scinticor angiographic system for a collimator system having only a lead base structure. As can be seen in FIG. 5A, there are two prominent peaks sensed, one peak at about 75 KeV associated with the lead K-alpha inelastically scattered X-rays 36 and the second cobalt gamma ray peak at about 140 KeV. The nearly equal prominence of the intensity of the two peaks points out the significance of removing the inelastic scattered X-rays 36. In FIG. 5B is shown the energy spectrum detected employing the collimator assembly 10 with substantially identical collimator dimensions.

As demonstrated by the data of FIG. 5, the collimator assembly 10 is highly effective in the removal of the lead K-alpha inelastic scattered X-rays 36, thus enabling the detector 34 to sense only the desired gamma ray portion 30. Consequently, the efficiency of detection for a given radionuclide source intensity in the specimen 28 can be substantially enhanced. As determined by actual experiment in Scinticor angiographic systems this is about 50 percent for the illustrated embodiment wherein the number of 140 KeV events detected increases, for example, from about 400,000 to 600,000 counts per second. Such an improvement in efficiency also results in enhanced signal which manifests itself as improved image resolution of the specimen cardiac system. For example, as shown by the angiographic image data of FIG. 6, a cardiologist is now able to resolve critical features previously unresolvable. The use of the collimator assembly 10 has, however, substantially improved resolution such that high quality first pass angiography can now be performed routinely. As shown in FIG. 6 the resulting images are of high quality, enabling a cardiologist to more effectively perform diagonses previously made without the benefit of such detailed medical information.

Preferably, the tin layer 22 does not have too high an atomic number, or the thin layer 22 can itself reemit a high energy X-ray which could be transmitted through the thin layer 22 and be sensed by the detector 34. Knowing the composition of the base structure 20, one can apply conventional radiation absorption knowledge and methods to determine the appropriate materials and their layer thicknesses necessary to absorb a substantial fraction of any inelastic scattered radiation, particularly emitted K alpha and L alpha X-rays from the base collimator structure 20. This basic concept of layered wall collimators can be applied to any radiation collimator, such as for X-rays, ions, infrared laser light, positrons, electrons, neutrons and microwave or other photon energies. Associated with each of these radiations is a known, developed knowledge of absorption and inelastic scattering events. In those instances in which inelastic scattered radiation can be produced, such unwanted data can be preferentially removed in the manner described.

The efficiency of the gamma ray collimator assembly 10 can be assessed with reasonable accuracy for the square cross section collimator geometry illustrated in FIG. 3. The efficiency is expressed in terms of the spatial dimensions:

$E = A_1 A_2 / 4\pi^2 M^2$ $A_1$=area of lead square (edge "b" squared)

$A_2$=area of tin square (edge "a" squared)

l=longitudinal length of collimator passageway (see FIG. 2)

M=center to center spacing (see FIG. 2 )

Thus, one can select a desired efficiency by adjusting the various geometries of the collimator assembly 10.

In another aspect of the invention the collimator assembly 10 can be constructed of any desired height and longitudinal length l, along the collimator assembly 10. The user can then assemble a final collimator assembly 10 of any desired length of longitudinal passageway by stacking two or more different height collimator assemblies.

While preferred embodiments of the invention have been shown and described, it will be clear to those skilled in the art that various changes and modifications can be made without departing from the invention in its broader aspects as set forth in the claims provided hereinafter.

I claim:

1. A collimator assembly for detecting selected radiation from a specimen under inspection, comprising a plurality of collimator elements wherein each of said collimator elements comprises walls defining an elongated longitudinal passageway, said walls absorbing divergent portions of said selected radiation from said specimen and said walls comprised of a first material covered by an inner layer of a second material adjacent the longitudinal passageway, said second material having a large absorption coefficient for radiation received from said specimen and inelastically scattered from said first material.

2. A method of collimating and detecting ionizing electromagnetic gamma radiation, comprising the steps of:

selecting a particular energy gamma radiation for collimation, said gamma radiation being output from a specimen of interest;

positioning a gamma radiation detector in a location facing open ends of a collimator to gather information about said specimen; and using said collimator to effectively remove radiation, interacting with said collimator, and said collimator having a plurality of collimator elements each having an open longitudinal passageway between the open ends of said collimator and each of said collimator elements, further having a wall structure of layers parallel to a longitudinal axis passing through the center of the open longitudinal passageway and divergent portions of said gamma radiation interacting with said layered wall structure, giving rise to inelastically scattered electromagnetic radiation of less energy than said gamma radiation and said inelastically scattered radiation being effectively removed by said layered wall structure, thereby allowing only said particular energy gamma radiation not interacting with said wall structure to pass undisturbed down the longitudinal passageway and out the open ends and be detected by said gamma radiation detector.

3. The method as defined in claim 2 wherein said collimator comprises a first thin layer material disposed nearest the non divergent portion of said particular energy gamma radiation passing through said longitudinal passageway with said first layer material having a high preferential absorption for said inelastic scattered radiation.

4. The method as defined in claim 2 wherein said layered wall structure comprises a thin tin layer on a base structure of lead.

5. A method of constructing a gamma ray collimator system, comprising the steps of:

assembling a plurality of base lead collimator elements having longitudinal passageways with longitudinal axes and open ends for allowing entry into and transmission of gamma rays from the passageway;

disposing a thin layer of tin on said lead collimator with said layer of tin being parallel to the longitudinal axes of the longitudinal passageways, said layer of tin being thick enough to effectively remove inelastic scattered high energy photons arising from gamma rays deviating from the open, longitudinal passageways and interacting with said base collimator elements; and positioning a gamma ray detector facing the open ends of said plurality of base lead collimator elements, each of said elements having said layer of tin parallel to the longitudinal axes which are substantially facing the open ends of said base lead collimator elements.

6. The method as defined in claim 5 further including the steps of stacking layers of said assembled collimator elements to form a desired length of longitudinal passageway for said collimator elements to collimate said gamma rays.

7. The method as defined in claim 6 wherein selected ones of said stacked layers further include an inserted egg crating matrix with each longitudinally extending wall of said matrix comprised of a lead center portion with a thin inner tin layer disposed thereon.

8. The method as defined in claim 5 further including the step of inserting an egg crating matrix into said plurality of collimator elements to provide additional resolution.

9. The method as defined in claim 8 wherein each said collimator element comprises a square lead tubing element and a square tin tubing element.

10. The method as defined in claim 8 wherein the longitudinal axes are perpendicular to the open ends of said base lead collimator elements.

11. A method of detecting undisturbed, selected gamma radiation using a radiation detector, comprising the steps of:

outputting a particular energy of said selected gamma radiation from a specimen under inspection;

inputting said particular energy gamma radiation into a plurality of collimator elements wherein each of said collimator elements comprises a layered wall defining an elongated longitudinal passageway having open ends through which undisturbed portions of said radiation enters and leaves, the planes of said layered wall being symmetrically disposed about a central longitudinal axis in each said collimator element and said layered wall absorbing the portion of said particular energy radiation diverging from the central longitudinal axis and interacting with said layered wall to generate inelastically scattered radiation with said layered wall comprised of a first material covered by an inner layer of a second material adjacent to the longitudinal passageway, said second material effectively removing said inelastically scattered radiation having less energy than said particular selected radiation; and sensing said undisturbed radiation output from the open ends of said collimator facing said radiation detector, and the planes of said layered wall being symmetrically disposed about the mean angle of said undisturbed radiation passing through the longitudinal passageway of each said collimator element.

12. The method as defined in claim 11 wherein said layered wall structure comprises a layer of tin on a layer of lead.

13. The method as defined in claim 11 wherein each said collimator element comprises a square shaped cross section perpendicular to the longitudinal passageway.

14. A method of detecting undisturbed, selected gamma radiation using a radiation detector, comprising the steps of:

outputting a particular energy of said selected gamma radiation from a specimen under inspection;

inputting said particular energy radiation into a plurality of collimator elements wherein each of said collimator elements comprises a layered wall defining an elongated longitudinal passageway having open ends through which undisturbed portions of said radiation enters and leaves, the planes of said layered wall being parallel to a central longitudinal axis in each said collimator element and said layered wall absorbing the portion of said particular energy radiation diverging from the central longitudinal axis and interacting with said layered wall to generate inelastically scattered radiation with said layered wall comprised of a first material covered by an inner layer of a second material adjacent to the longitudinal passageway, said second material effectively removing said inelastically scattered radiation having less energy than said particular selected radiation; and sensing said undisturbed radiation output from the open ends of said collimator facing said radiation detector, and the planes of said layered wall being substantially parallel to the mean angle of said undisturbed radiation passing through the longitudinal passageway of each said collimator element.

15. The method as defined in claim 14 wherein said layered wall structure comprises a layer of tin on a layer of lead.

16. The method as defined in claim 14 wherein said collimator elements can be stacked to construct longer collimators.

* * * * *